(12) United States Patent
Crespi

(10) Patent No.: US 8,452,395 B2
(45) Date of Patent: May 28, 2013

(54) BATTERY LONGEVITY ESTIMATOR THAT ACCOUNTS FOR EPISODES OF HIGH CURRENT DRAIN

(75) Inventor: Ann M. Crespi, Mobile, AL (US)

(73) Assignee: Medtronic, Inc., Minneapolis, MN (US)

( * ) Notice: Subject to any disclaimer, the term of this patent is extended or adjusted under 35 U.S.C. 154(b) by 83 days.

(21) Appl. No.: 12/830,748

(22) Filed: Jul. 6, 2010

(65) Prior Publication Data

US 2012/0010672 A1 Jan. 12, 2012

(51) Int. Cl.
*A61N 1/3956* (2006.01)
*A61N 1/3708* (2006.01)
*A61N 1/20* (2006.01)
*G01R 21/33* (2006.01)

(52) U.S. Cl.
USPC .................... 607/5; 607/29; 607/75; 702/62

(58) Field of Classification Search
USPC .................... 607/5, 29, 75; 702/62
See application file for complete search history.

(56) References Cited

U.S. PATENT DOCUMENTS

| | | |
|---|---|---|
| 4,556,061 A | 12/1985 | Barreras et al. |
| 4,715,381 A | 12/1987 | Moberg |
| 5,117,824 A | 6/1992 | Keimel et al. |
| 5,137,020 A | 8/1992 | Wayne et al. |
| 5,391,193 A | 2/1995 | Thompson |
| 5,402,070 A | 3/1995 | Shelton et al. |
| 5,458,624 A | 10/1995 | Renirie et al. |
| 5,620,474 A | 4/1997 | Koopman |
| 5,741,307 A | 4/1998 | Kroll |
| 5,800,472 A | 9/1998 | Mann |
| 6,108,579 A | 8/2000 | Snell et al. |
| 6,167,309 A | 12/2000 | Lyden |
| 6,344,730 B1 | 2/2002 | Rohrböck et al. |
| 6,400,988 B1 | 6/2002 | Gurewitsch |
| 6,671,552 B2 | 12/2003 | Merritt et al. |
| 6,901,293 B2 | 5/2005 | Rogers et al. |
| 2002/0161328 A1 | 10/2002 | Rogers |
| 2003/0065366 A1 | 4/2003 | Merritt et al. |
| 2004/0024426 A1 | 2/2004 | Lyden |
| 2004/0199146 A1 | 10/2004 | Rogers et al. |
| 2005/0007073 A1 | 1/2005 | James et al. |
| 2005/0088145 A1 | 4/2005 | Loch |
| 2005/0256548 A1 | 11/2005 | Rogers et al. |
| 2008/0097544 A1* | 4/2008 | Gandhi et al. .................. 607/29 |
| 2008/0177345 A1 | 7/2008 | Schmidt et al. |

FOREIGN PATENT DOCUMENTS

| | | |
|---|---|---|
| WO | WO 2008/121110 A1 | 10/2008 |
| WO | WO 2009/091407 A2 | 7/2009 |
| WO | WO 2010/005806 A2 | 1/2010 |
| WO | WO 2011/005152 A1 | 1/2011 |

OTHER PUBLICATIONS

International Search Report and Written Opinion for PCT/US2011/040179.

* cited by examiner

*Primary Examiner* — Nicole F Lavert

(57) ABSTRACT

System and method for estimating a remaining capacity of a battery of an implantable medical device. The implantable medical device has a battery producing a current and having a remaining battery capacity, the implantable medical device being configured to utilize a relatively low amount of the current and, in specific instances, a relatively large pulse of the current. The processor is coupled to the battery and configured to calculate an estimate of the remaining battery capacity based, at least in part, on a measured battery parameter and occurrences of the specific instances of delivery of the relatively large pulse of the current.

26 Claims, 4 Drawing Sheets

BATTERY LONGEVITY ESTIMATOR THAT ACCOUNTS FOR EPISODES OF HIGH CURRENT DRAIN

BACKGROUND

Implantable medical devices such as cardioverter/defibrillators are commonly configured to treat cardiac arrhythmias by delivering high voltage energy pulses to cardiac tissue. Implantable defibrillators commonly delivery therapy by way of electrodes positioned within or near the heart of the patient. Such therapy includes defibrillation therapy, which utilizes a sudden, high energy pulse designed to shock the heart of the patient out of a cardiac arrhythmia if and when a cardiac arrhythmia occurs. Implantable defibrillators also commonly incorporate pacing therapy, which utilizes very low energy pulses designed to trigger cardiac contractions in lieu of an adequately frequent natural heart beat of the patient.

Implantable defibrillators commonly incorporate a power source, such as a battery, which provides operational power to the componentry of the defibrillator, including electronics which manage the function of the device, monitor the condition of the patient in which the device is implanted and deliver therapy to the patient. Many or most device functions operate effectively continually, such as sensing the cardiac condition of the patient, or frequently, such as cardiac pacing therapy delivery in certain patients, and thus account for steady, predictable and, usually, low-level drains on the battery capacity. Defibrillation therapy, by contrast, usually occurs very infrequently in most patients, commonly with months or years between defibrillation therapy deliveries, owing to the generally infrequent occurrence of arrhythmias which require treatment. As such, defibrillation therapy is, from a standpoint of battery management, a large, sudden, essentially random drain on the battery of the implantable defibrillator.

Because implantable defibrillators often provide life-sustaining therapy to the patients in which they are implanted, it may be essential to the well-being of the patient to understand how long the battery may be expected to last until the battery will be discharged to a point of being unable to provide reliable therapy. It is known in the art that the terminal voltage of batteries often utilized in implantable defibrillators typically corresponds, to some degree, to the remaining charge in the battery. For instance, as the remaining charge decreases, the terminal voltage likewise decreases. However, the terminal voltage may not, and often does not, correspond to the remaining charge in the battery in a wholly straight-forward and predictable relationship.

SUMMARY

In particular, it has been discovered that, while relatively steady current drain on a battery may result in a relatively predictable and accurate relationship between terminal voltage and remaining charge, a steady current drain coupled with occasional sudden, large current drains may reduce the accuracy of the relationship between terminal voltage and remaining charge. The impact on the accuracy in the prediction of remaining charge of a battery based on the relationship between terminal voltage and the remaining charge may be relatively short in duration, but has been shown to impart some lasting impact. A sudden, large current drain on top of an underlying low-level current drain has been shown to skew the terminal voltage to remaining charge relationship such that the terminal voltage consistently measures relatively lower than would be anticipated in view of the remaining charge in the battery.

The skew in the terminal voltage-remaining charge relationship may, as a result, cause a battery to be evaluated as being low on charge and in need of replacement or recharging some time after having an actual remaining charge sufficiently low to justify such an evaluation. Moreover, the skew to the relationship between terminal voltage to remaining charge has been shown to be relatively larger soon after a large current drain than relatively longer periods of time after the large current drain. Such variation may further detract from the reliability of battery measurements based only on terminal voltage.

The impact of high current drain arising from the delivery of defibrillation pulses has been mitigated by adjusting battery terminal calculations in two important ways. First, incorporated into a battery terminal calculation is an adjustment accounting for a number of times high-current drain events occur. It has been determined that the adjustment may factor in both an amount of charge utilized during the high-current event and an original available charge of the battery at a time of manufacture or otherwise early in the life of the battery. Second, analyses of remaining charge of the battery are spread out over relatively long periods of time to mitigate the relatively greater influence of short-term variance to the terminal voltage-remaining charge relationship.

In an embodiment, a system comprises an implantable medical device and a processor. The implantable medical device has a battery producing a current and having a remaining battery capacity, the implantable medical device configured to utilize a relatively low amount of the current and, in specific instances, a relatively large pulse of the current. The processor is operatively coupled to the battery and configured to calculate an estimate of the remaining battery capacity based, at least in part, on a measured battery parameter and occurrences of the specific instances of delivery of the relatively large pulse of the current.

In an embodiment, the processor is configured to calculate the estimate of the remaining battery capacity further based, at least in part, on the measured battery parameter and a number of occurrences of the specific instance of deliver of the relatively large pulse of the current.

In an embodiment, the processor is configured to calculate the estimate of the remaining battery capacity further based, at least in part, on the measured battery parameter, and then to decrease the estimate of the remaining battery capacity based, at least in part, on the number of occurrences of the specific instances of delivery of the relatively large pulse of the current.

In an embodiment, the processor is configured to calculate the estimate of the remaining battery capacity further based, at least in part, on a function of the number of occurrences of the specific instances of delivery of delivery of the relatively large pulse of the current, an amount of charge utilized in the relatively large pulse of current and an original charge of the battery.

In an embodiment, the processor is configured to calculate the estimate of the remaining battery capacity based, at least in part, on the number of occurrences multiplied by a ratio of the charge utilized in the relatively large pulse of current and the original charge of the battery.

In an embodiment, the processor is configured to adjust the estimate of the remaining battery capacity based, at least in part, on a function of the remaining battery capacity measured over a period of time.

In an embodiment, the period of time is at least one week

In an embodiment, the period of time is at least two weeks.

In an embodiment, the period of time is at least four weeks.

In an embodiment, the period of time is at least twelve weeks.

In an embodiment, the period of time is at least twenty-six weeks.

In an embodiment, the function is an average of a plurality of the remaining battery capacity measurements taken during the period of time.

In an embodiment, the measured battery parameter is a battery output voltage.

In an embodiment, the processor is a component of the implantable medical device.

In an embodiment, the system further comprises an external device comprising the processor.

In an embodiment, a method is disclosed for estimating a remaining battery capacity of a battery of an implantable medical device configured to utilize a relatively low amount of the current and, in specific instances, a relatively large pulse of the current, the method utilizing a processor. The method comprises the step of calculating an estimate of the remaining battery capacity based, at least in part, on a measured battery parameter and occurrences of the specific instances of delivery of the relatively large pulse of the current.

FIGURES

DETAILED DESCRIPTION

Figure 1:
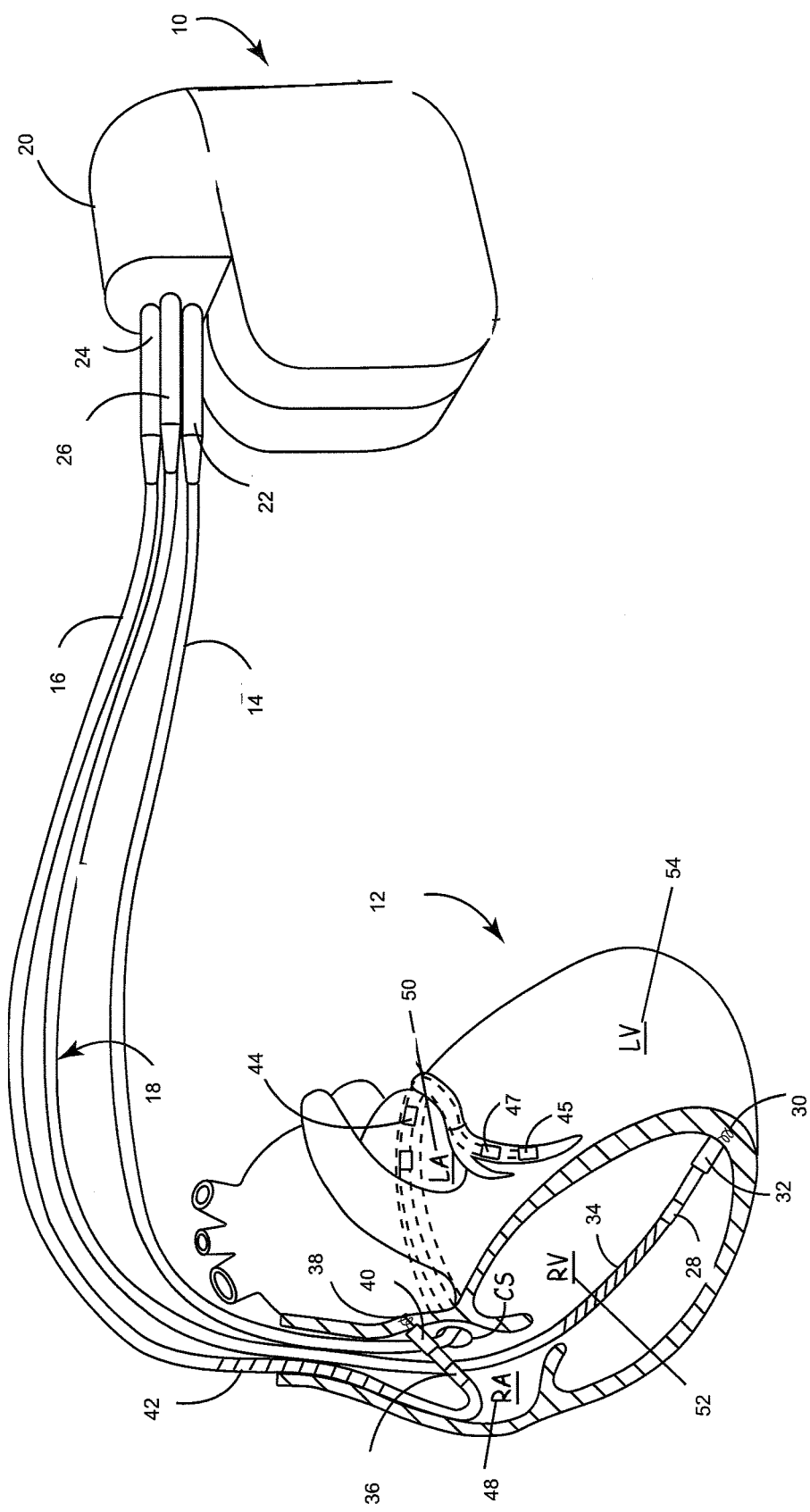
FIG. 1 is a view of an implantable cardioverter defibrillator.

FIG. 1 is an illustration of implantable medical device 10 implanted in a patient. In the illustrated embodiment, implantable medical device 10 is a cardiac defibrillator with a pacing function. The pacing function may treat bradycardia and may resynchronize heart 12 in conditions of patient heart failure. Such a defibrillator is known as a cardiac resynchronization therapy defibrillator, known in the art as a CRT-D device. In various alternative embodiments, implantable medical device 10 may be a cardioverter/defibrillator without a pacing function or with a pacing function but without a cardiac resynchronization feature. In addition, implantable medical device 10 may be any device which incorporates high current draws from a battery. Implantable medical device 10 is coupled to heart 12 by way of coronary sinus lead 14, right atrial lead 16, and right ventricular lead 18. Connector block 20 receives connectors 22, 24 and 26 positioned on the proximal ends of coronary sinus lead 14, right atrial lead 16 and right ventricular lead 18, respectively, and provides electrical connectivity between leads 14, 16, 18 and electronic circuitry within implantable medical device 10.

In the illustrated embodiment, ring electrode 28, extendable helix electrode 30 mounted retractably within an electrode head 32, and coil electrode 34 are positioned on right ventricular lead 18 and are electrically coupled to an insulated conductor within right ventricular lead 18. As illustrated, right ventricular lead 18 is positioned such that its distal end is in the right ventricle for sensing right ventricular cardiac signals and delivering pacing or shocking pulses in the right ventricle. The proximal end of the insulated conductors are coupled to corresponding connectors carried by bifurcated connector 26 for providing electrical connection to implantable medical device 10.

Right atrial lead 16 may include ring electrode 36 and extendable helix electrode 38, mounted retractably within electrode head 40, for sensing and pacing in the right atrium. Right atrial lead 16 may further include coil electrode 42 to deliver high-energy shock therapy. Right atrial lead 16 may be positioned such that its distal end is in the vicinity of the right atrium and the superior vena cava. Ring electrode 36, helix electrode 38 and coil electrode 42 may each be connected to an insulated conductor within the body of right atrial lead 16. The insulated conductor may be coupled at its proximal end to bi-furcated connector 24.

Coronary sinus lead 14 may include defibrillation coil electrode 44 that may be used in combination with coil electrode 34 or coil electrode 42 for delivering electrical shocks for cardioversion and defibrillation therapies. Coronary sinus lead 14 may be advanced within the vasculature of the left side of heart 12 via the coronary sinus and great cardiac vein. In various embodiments, coronary sinus lead 14 may also be include a distal tip electrode 45 and ring electrode 47 for pacing and sensing functions in the left chambers of the heart. Coil electrode 44 is coupled to an insulated conductor within the body of lead 14. The insulated conductor may be coupled at its proximal end to connector 22.

Electrodes 28, 30, 36 and 38 may be used to form bipolar pairs. Various ones of such bipolar pairs may be referred to as a "tip-to-ring" pairs. Electrodes 28, 30, 36 and 38 may likewise be utilized individually in unipolar configuration with implantable medical device housing 46 serving as an indifferent electrode, commonly referred to as the "can" or "case" electrode. Housing 46 may also serve as a subcutaneous defibrillation electrode in combination with one or more of coil electrodes 34, 42 and 44 for defibrillation of atria 48, 50 or ventricles 52, 54 of heart 12. In various embodiments, alternate lead systems may be substituted for the lead system of the embodiment of FIG. 1. Leads for use with single chamber, dual chamber, or multichamber implantable medical devices may be utilized.

Figure 2:
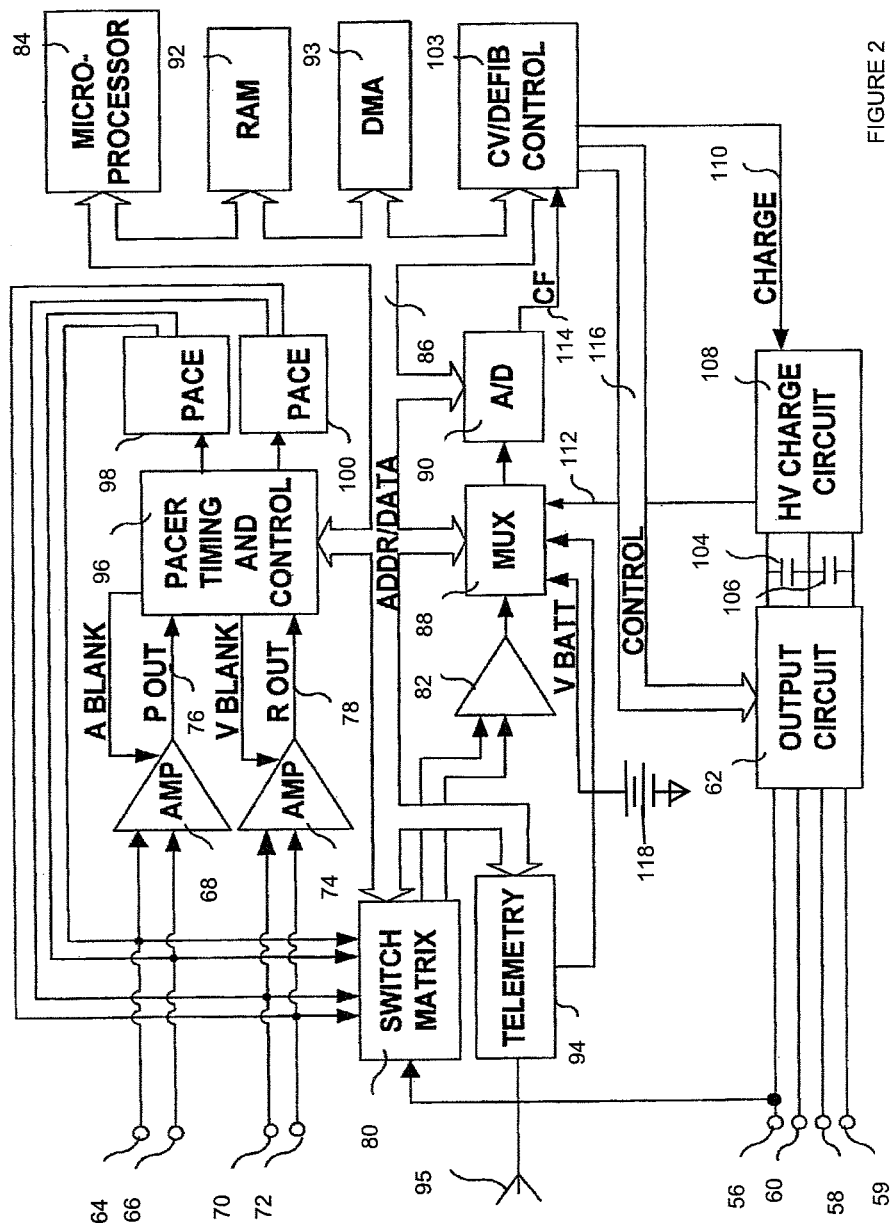
FIG. 2 is a functional schematic diagram of the implantable cardioverter defibrillator of FIG. 1.

FIG. 2 is a functional schematic diagram of implantable medical device 10. Connection terminal 56 provides electrical connection to the housing 46 for use as the indifferent electrode during unipolar stimulation or sensing. Connection terminals 58, 59 and 60 provide electrical connection to coil electrodes 44, 42 and 34 respectively. Each of connection terminals 56, 58, 59 and 60 are coupled to the high voltage output circuit 62 to facilitate the delivery of high energy shocking pulses to heart 12 using one or more of coil electrodes 34, 42 and 44, and, in an embodiment, housing 46.

Connection terminals 64 and 66 provide electrical connection to helix electrode 38 and ring electrode 36 positioned in the right atrium, respectively. Connection terminals 64 and 66 are further coupled to atrial sense amplifier 68 for sensing cardiac signals originating from the atrium of heart 12. Such signals include atrial depolarizations and are commonly recognized as P-waves in electrocardiograms. Connection terminals 70 and 72 provide electrical connection to the helix electrode 30 and the ring electrode 28, respectively. Connection terminals 70 and 72 are further coupled to a ventricular sense amplifier 74 for sensing ventricular signals.

Atrial sense amplifier 68 and ventricular sense amplifier 74 may take the form of automatic gain controlled amplifiers with adjustable sensing thresholds. In an embodiment, the general operation of ventricular sense amplifier 74 and atrial sense amplifier 68 may correspond to that disclosed in U.S. Pat. No. 5,117,824, by Keimel, et al., incorporated herein by reference in its entirety. When a signal received by atrial sense amplifier 68 exceeds an atrial sensing threshold, a signal may be generated on P-out signal line 76. When a signal received by ventricular sense amplifier 74 exceeds a ventricular sensing threshold, a signal may be generated on R-out signal line 78 to indicate a sensing of a ventricular depolarization.

In an embodiment, switch matrix 80 is used to select which of electrodes 28, 30, 34, 36, 38, 42, 44 are coupled to wide band amplifier 82 for use in digital signal analysis. Selection of various ones of electrodes 28, 30, 34, 36, 38, 42, 44 may be controlled by microprocessor 84 via data/address bus 86 in order to create an electrode configuration. The electrode configuration may be varied as desired for the various sensing, pacing, cardioversion and defibrillation functions of implantable medical device 10. Signals from the electrodes selected for coupling to bandpass amplifier 82 may be provided to multiplexer 88, and thereafter converted to multi-bit digital signals by A/D converter 90, for storage in random access memory 92 under control of direct memory access circuit 93. Microprocessor 84 may employ digital signal analysis techniques to characterize the digitized signals stored in random access memory 92 to recognize and classify the heart rhythm employing any of the numerous signal processing methodologies known in the art.

In an embodiment, upon detection of an arrhythmia, data obtained from electrodes 28, 30, 34, 36, 38, 42, 44, including electrograms, sensed intervals and corresponding annotations of sensed events, may be stored in random access memory 92. The electrogram signals stored may be sensed from programmed near-field and/or far-field sensing electrode pairs. A near-field sensing electrode pair includes, in an embodiment, a tip electrode and a ring electrode located in an atrium 48, 50 or a ventricle 52, 54, such as electrodes 36 and 38 or electrodes 28 and 30. A far-field sensing electrode pair may, in various embodiments, include any of the following exemplary combinations: any pair of defibrillation coil electrodes 32, 42, 44; any of defibrillation coil electrodes 32, 42, 44 with housing 46; tip electrode 30, 38 with housing 46; tip electrode 30, 38 with a defibrillation coil electrode 34, 42; or atrial tip electrode 38 with ventricular ring electrode 28. Additional electrode combinations may be utilized.

In various alternative embodiments, implantable medical device 10 may utilize leads and electrodes which are positioned outside of the thoracic cavity of the patient. In such embodiments, the electrodes may sense far-field cardiac signals, in contrast to the near-field signals sensed by electrodes 28, 30, 34, 36, 38, 42, 44 positioned in or close to heart 12. An implantable medical device 10 which incorporates leads and electrodes outside of the thoracic cavity of the patient is known in the art as a subcutaneous implantable cardioverter defibrillator, and may deliver defibrillation therapy to heart 12 in a manner related to that of conventional defibrillators described above.

Telemetry circuit 94 may receive downlink telemetry from and may send uplink telemetry to an external programmer, as is conventional in implantable medical devices, by means of antenna 95. Data to be uplinked to the programmer and control signals for the telemetry circuit may be provided by microprocessor 84 via address/data bus 86. Electrogam data that has been stored upon arrhythmia detection or as triggered by other monitoring algorithms may be uplinked to an external programmer using telemetry circuit 94. Received telemetry may be provided to microprocessor 84 via multiplexer 88. Numerous types of telemetry systems known in the art for use in implantable devices may be used.

Pacer timing and control circuitry 96 includes programmable digital counters which control the basic time intervals associated with various single, dual or multi-chamber pacing modes or anti-tachycardia pacing therapies delivered in the atria or ventricles. Pacer circuitry 96 also determines the amplitude of the cardiac pacing pulses under the control of microprocessor 84.

During pacing, escape interval counters within pacer timing and control circuitry 96 may be reset upon sensing of atrial and ventricular depolarizations, i.e., P-waves and R-waves, as indicated by signals on lines 76 and 78, respectively. In accordance with the selected mode of pacing, pacing pulses are generated by atrial pacer output circuit 98 and ventricular pacer output circuit 100. The pacer output circuits 98 and 100 are coupled to the desired electrodes for pacing via switch matrix 80. The escape interval counters are reset upon generation of pacing pulses, and thereby control the basic timing of cardiac pacing functions, including anti-tachycardia pacing.

The durations of the escape intervals may be determined by microprocessor 84 via data/address bus 86. The value of the count present in the escape interval counters when reset by sensed R-waves or P-waves can be used to measure R-R intervals and P-P intervals for detecting the occurrence of a variety of arrhythmias.

Microprocessor 84 includes associated ROM in which stored programs controlling the operation of the microprocessor 84 reside. A portion of the random access memory 92 may be configured as a number of recirculating buffers capable of holding a series of measured intervals for analysis by the microprocessor 84 for predicting or diagnosing an arrhythmia.

In response to the detection of tachycardia, anti-tachycardia pacing therapy can be delivered by loading a regimen from microcontroller 84 into the pacer timing and control circuitry 96 according to the type of tachycardia detected. In the event that higher voltage cardioversion or defibrillation pulses are required, microprocessor 84 activates the cardioversion and defibrillation control circuitry 102 to initiate charging of high voltage capacitors 104 and 106 via charging circuit 108 under the control of high voltage charging control line 110. The voltage on the high voltage capacitors is monitored via voltage capacitor line 112, which is passed through the multiplexer 88. When the voltage reaches a predetermined value set by microprocessor 84, a logic signal is generated on the capacitor full line 114, terminating charging. The defibrillation or cardioversion pulse is delivered to the heart under the control of the pacer timing and control circuitry 96 by an output circuit 62 via control bus 116. The output circuit 62 determines the electrodes used for delivering the cardioversion or defibrillation pulse and the pulse wave shape.

Battery 118 provides power to operate the electrical componentry of implantable medical device 10. The electrical componentry includes, but is not limited to, microprocessor 84, RAM 92, telemetry module 94, pacer timing and control 96 cardioversion/defibrillation control 102 and high voltage charge circuit 108. In various embodiments, battery 118 is selected from conventional implantable medical device battery chemistries, including nickel-cadmium and lithium-ion, though alternative chemistries may be utilized.

Figure 3:
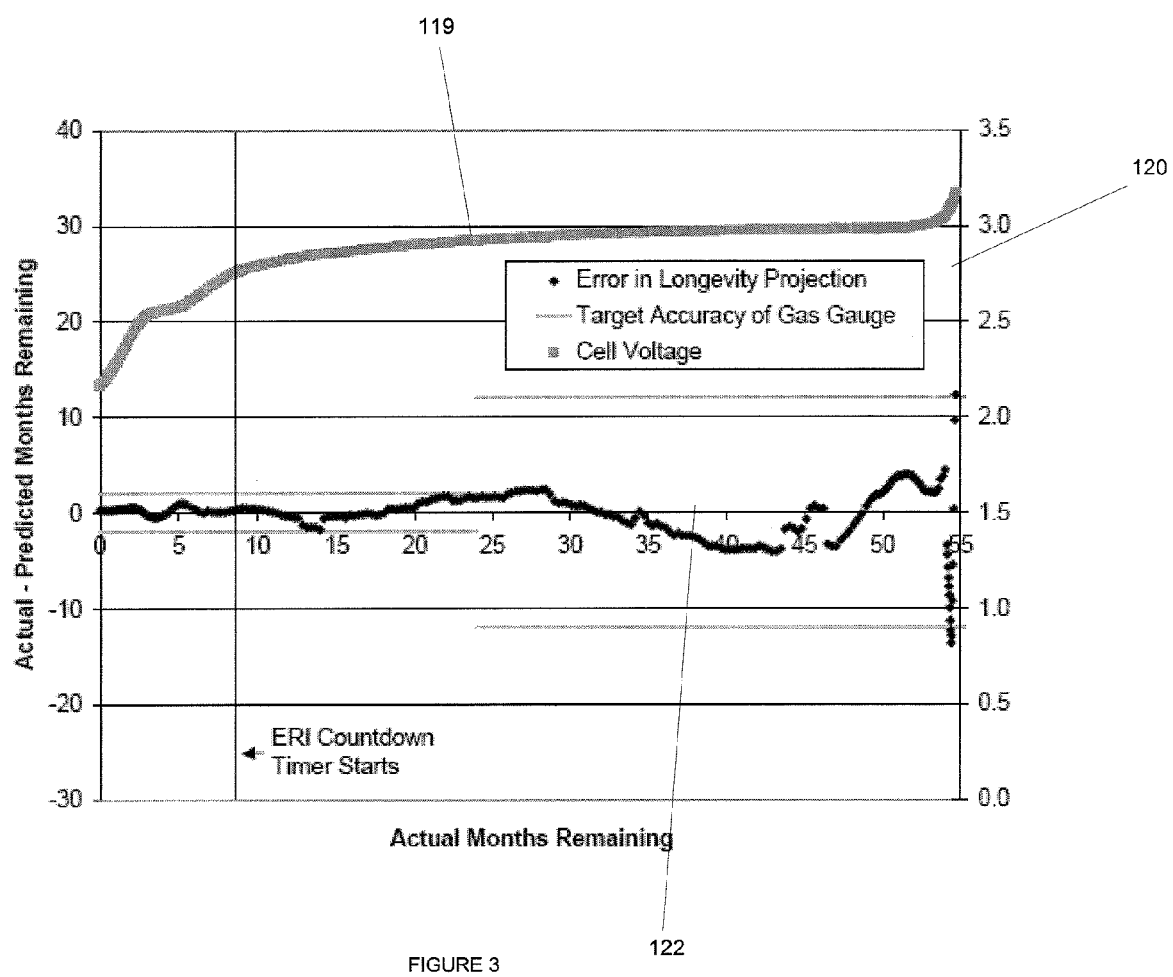
FIG. 3 is a graphical representation of a relationship between a charge remaining and a terminal voltage of a battery of an implantable medical device.

FIG. 3 is a graphical representation of a conventional relationship 119 between terminal voltage 120 of battery 118 and remaining capacity 122 of battery 118. In various embodiments, battery 118 generates terminal voltage 120 of approximately 3.2 volts when battery 118 has a full charge, i.e. remaining charge 122 equals a full capacity of battery 118. As remaining charge 122 of battery 118 degrades terminal voltage 120 may also degrade. However, terminal voltage 120 may not degrade linearly with the degradation of remaining charge 122. In particular, battery 118 may maintain terminal voltage 120 of approximately three (3) volts, plus-or-minus approximately 0.25 volts, over much of the operational life of battery 118. In an embodiment, when the remaining charge of battery 118 falls below approximately 15% of its original charge, the terminal voltage may be less than approximately 2.75 volts, at which point implantable medical device 10 may indicate that battery 118 is in need of replacement, such as by replacing implantable medical device 10 as a whole or by replacing battery 118 itself, or that battery 118 is in need of recharging in embodiments which incorporate recharging circuitry.

According to the above estimates for remaining charge 122, average current delivered from battery 118 is computable as the change in battery charge over time, or:

$$I_{ave} = dQ/dt. \quad \text{Equation 1:}$$

A measurement of terminal voltage of battery 118 at a first time may be arrived at, then, according to:

$$V_1 = f(Q_1, Q_1/t_1) \quad \text{Equation 2:}$$

And a second measurement of terminal voltage of battery 118 at a second time may be defined as:

$$V_2 = f(Q_2, (Q_2 - Q_1)/(t_2 - t_1)) \quad \text{Equation 3:}$$

In various embodiments, terminal voltage 120 is sufficient to arrive at an adequately accurate estimate of remaining capacity 122. However, according to the relationship of Equation 3, in alternative embodiments, relatively more accurate assessments of remaining capacity 122 may be arrived at by solving for different values of charge remaining. In such embodiments, implantable medical device 10 calculates remaining capacity 122 not directly according to terminal voltage 120, but rather according to multiple factors pertaining to battery 118.

In an embodiment, a percentage of the inverse of remaining capacity 122, known as a "depth of discharge" is estimated according to various battery parameters. In the recursive formula, a prior total charge delivered $Q_{last}$ by battery 118 is added to an estimated charge delivered since the previous recursive application of the formula of a total charge delivered from battery 118 over a period of time $dQ_{est}$ and divided by an original charge $Q_{max}$ of battery 118 at a time at or near a manufacture of battery 118. In an embodiment, $dQ_{est}$ is proportional to a current delivered from battery 118 over a predetermined timeframe. Calculation of the depth-of-discharge estimate may be represented according to Equation 4:

$$DOD_{est} = (Q_{last} + dQ_{est})/Q_{max} \quad \text{Equation 4:}$$

It has been discovered, however, that high-current therapy, such as delivery of defibrillation energy, may result in a skew to the depth-of-discharge estimate which may last throughout the life of battery 118. In particular, the depth of discharge estimate as calculated by Equation 4 may be relatively too low (i.e., battery 118 may have more capacity remaining than would be suggested by the depth-of-discharge estimate) if implantable medical device 10 delivers defibrillation therapy to heart 12, owing to an incremental change in the chemistry of battery 118 for each defibrillation pulse delivered. Specifically, the delivery of a single defibrillation pulse may tend to skew $DOD_{est}$ according to Equation 1 by a value approximately equal to an amount of charge delivered in a defibrillation pulse $Q_{perCharge}$ as a percentage of original battery capacity $Q_{max}$. $Q_{perCharge}$ may vary on the basis of frequency, current and duration of the defibrillation pulse. As such, Equation 4 may be modified into Equation 5 below, which may be utilized to obtain an estimated depth-of-discharge which accounts for a number of times N defibrillation therapy has been delivered. In various embodiments, defibrillation therapy may incorporate charge delivery from approximately 7.5 milliampere-hours to approximately 10.0 milliampere-hours.

$$DOD_{estDefib} = (Q_{last} + dQ_{est})/Q_{max} + (N^* Q_{perCharge})/Q_{max} \quad \text{Equation 5:}$$

Equation 5 may be implemented in circumstances where an battery powered device has high-current drain situations in which charge from approximately 7.5 milliampere-hours to approximately 10.0 milliampere-hours is delivered over relatively short timeframes of approximately twenty (20) seconds or less. In alternative embodiments, the high-current drain range may be from approximately five (5) millampere-hours and higher.

Equation 5 may be applied iteratively over a time period to obtain a depth-of-discharge estimate which reflects multiple measurements of battery 118 characteristics over the time period. In various embodiments, Equation 5 may be applied iteratively more than twice. In an embodiment, Equation 5 is applied one thousand times to obtain a final depth-of-discharge estimate, or until a stability criteria is met. In an embodiment, a stability criteria is met if an estimated terminal voltage $V_{est}$ of battery 118 based on the measured output current of battery 118 and the estimated depth-of-discharge is within a threshold tolerance of a measured terminal voltage $V_{measured}$. In an embodiment, the threshold tolerance is 0.1 millivolts.

In an alternative embodiment, more than one stability criteria may be applied, including a difference between a maximum allowable current drain from battery 118 and the measured output current of battery 118 utilized to calculate the estimated terminal voltage $V_{est}$ above being less than a threshold current value. In an embodiment, the threshold current value is 0.01% of the maximum allowable current. In an embodiments, the maximum allowable current from battery 118 is approximately 0.4 amperes. In alternative embodiments, the maximum allowable current ranges from 0.3 amperes to 0.5 amperes. In an embodiment, if either the stability condition relating to measured terminal voltage or the difference between a maximum allowable current and the measured output current of battery 118 is met, or if the set number of iterations (one thousand, in the embodiment described above) is met, then the iterative application of Equation 5 is ceased.

In order to apply Equation 5 iteratively, a measurement may be taken of current delivered by battery 118 for each iteration during the time between the immediately preceding iteration and the current iteration. The current over time is applied as the change in charge over that time $dQ_{est}$ which is then applied into the new iteration of Equation 5. As reviewed above, Equation 5 may be applied iteratively with new values for $dQ_{est}$ until the stability conditions are met or the maximum number of iterations are met. The final, iteratively obtained value for the depth-of-discharge estimate may be applied to estimate a charge remaining of battery 118.

Even after an iterative estimate of the depth-of-discharge of battery 118, it may be advantageous, in certain embodiments, to base decisions regarding replacement of battery 118 not on a single, iterative estimate of the depth-of-discharge. Such an iterative estimate may be measured over seconds or minutes, even with one thousand iterations being conducted, and thus may nevertheless be susceptible to short-term transients on the chemistry of battery 118 arising from high-current drains on battery 118. In certain past embodiments which have not recognized the short-term nature of skew to charge remaining calculations of implantable medical device applications, some charge remaining estimates have been averaged over two-week periods.

However, based on contemporary battery chemistries and the present nature of high-current deliveries by battery 118, a two-week averaging of depth-of-discharge estimates may be susceptible to short-term skews arising out of the high-current delivery. As such, in various embodiments, depth-of-discharge measurements are averaged over time periods of greater than two weeks, such as four weeks. In various embodiments, depth-of-discharge measurements are measured over twelve-week moving windows. In an embodiment, depth-of-discharge measurements are averaged over twenty-six week moving windows. As such, the moving average of the depth-of-discharge estimates may be utilized to make decisions concerning a likely remaining time until battery 118 needs to be replaced or recharged.

Figure 4:
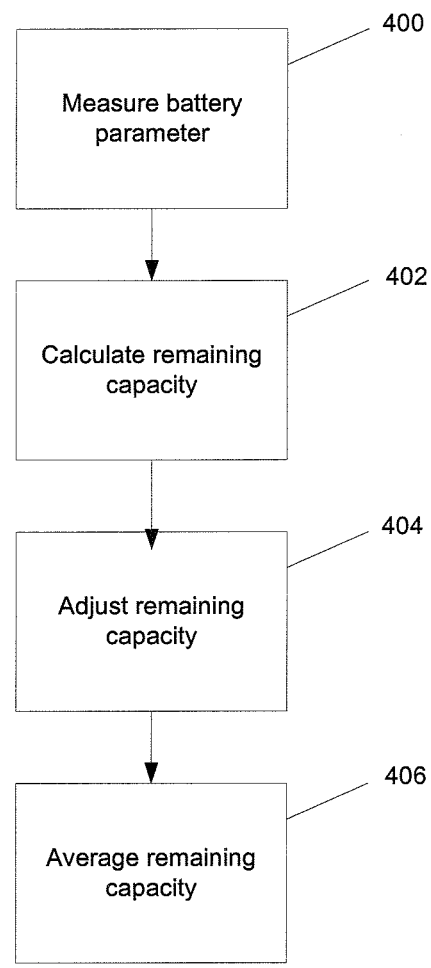
FIG. 4 is a flowchart for estimating a remaining capacity of a battery of an implantable medical device.

FIG. 4 is a flowchart of a method of estimating a remaining battery capacity of battery 118 of implantable medical device 10. A battery parameter is measured (400). As described above, the measured battery parameter may include the terminal voltage of battery 118 and a current delivered by battery 118. An estimate of the remaining battery capacity is calculated (402) based, at least in part, on the measured battery parameter. In various embodiments, the calculation is based on Equation 4 above, with the remaining battery capacity being based on the difference between the original charge of battery 118 $Q_{max}$ and the depth-of-discharge calculated in Equation 4 above. The charge remaining is then reduced (404) based, at least in part, on a number of occurrences of a relatively large pulse of current, such as a defibrillation pulse. In an embodiment, the effect of steps (402) and (404) is to implement Equation 5 above to determine $DOD_{estDefib}$, which may be converted into charge remaining of battery 118.

The estimate of remaining battery capacity is averaged (406) over a moving window in order to provide an averaged estimate of remaining battery capacity. As described above, the remaining battery capacity may be averaged over a window of at least two weeks. In various alternative embodiments, the window may be at least four weeks, twelve weeks or twenty-six weeks.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system, comprising:
an implantable medical device comprising a battery producing a current and having a remaining battery capacity, said implantable medical device configured to utilize a relatively low amount of said current and, in specific instances, a relatively large pulse of said current;
said system having a processor operatively coupled to said battery and configured to calculate an estimate of said remaining battery capacity based, at least in part, on a measured battery parameter and occurrences of said specific instances of delivery of said relatively large pulse of said current.

2. The system of claim 1 wherein said processor is configured to calculate said estimate of said remaining battery capacity further based, at least in part, on said measured battery parameter and a number of occurrences of said specific instance of delivery of said relatively large pulse of said current.

3. The system of claim 2 wherein said processor is configured to calculate said estimate of said remaining battery capacity further based, at least in part, on said measured battery parameter, and then to reduce said estimate of said remaining battery capacity based, at least in part, on said number of occurrences of said specific instances of delivery of said relatively large pulse of said current.

4. The system of claim 2 wherein said processor is configured to calculate said estimate of said remaining battery capacity further based, at least in part, on a function of said number of occurrences of said specific instances of delivery of delivery of said relatively large pulse of said current, an amount of charge utilized in said relatively large pulse of current and an original charge of said battery.

5. The system of claim 4 wherein said processor is configured to calculate said estimate of said remaining battery capacity based, at least in part, on said number of occurrences multiplied by a ratio of said charge utilized in said relatively large pulse of current and said original charge of said battery.

6. The system of claim 2 wherein said processor is configured to adjust said estimate of said remaining battery capacity based, at least in part, on a function of said remaining battery capacity measured over a period of time.

7. The system of claim 6 wherein said period of time is at least two weeks.

8. The system of claim 7 wherein said period of time is at least four weeks.

9. The system of claim 8 wherein said period of time is at least twelve weeks.

10. The system of claim 9 wherein said period of time is at least twenty-six weeks.

11. The system of claim 6 wherein said function is an average of a plurality of said remaining battery capacity measurements taken during said period of time.

12. The system of claim 2 wherein said measured battery parameter is a battery output voltage.

13. The system of claim 2 wherein said processor is a component of said implantable medical device.

14. The system of claim 2, further comprising an external device comprising said processor.

15. A method of estimating a remaining battery capacity of a battery of an implantable medical device configured to utilize a relatively low amount of said current and, in specific instances, a relatively large pulse of said current, the method utilizing a processor, comprising the step of:
calculating an estimate of said remaining battery capacity based, at least in part, on a measured battery parameter and occurrences of said specific instances of delivery of said relatively large pulse of said current.

16. The method of claim 15 wherein said calculating step calculates said estimate of said remaining battery capacity further based, at least in part, on said measured battery parameter and a number of occurrences of said specific instance of deliver of said relatively large pulse of said current.

17. The method of claim 16 wherein said calculating step calculates said estimate of said remaining battery capacity based, at least in part, on said measured battery parameter, said method then further comprising the step of:
reducing said estimate of said remaining battery capacity based, at least in part, on said number of occurrences of said specific instances of delivery of said relatively large pulse of said current.

18. The method of claim 16 wherein said calculating said estimate of said remaining battery capacity step is further based, at least in part, on a function of said number of occurrences of said specific instances of delivery of delivery of said relatively large pulse of said current, an amount of charge utilized in said relatively large pulse of current and an original charge of said battery.

19. The method of claim 18 wherein said calculating said estimate of said remaining battery capacity step is based, at least in part, on said number of occurrences multiplied by a ratio of said charge utilized in said relatively large pulse of current and said original charge of said battery.

20. The method of claim 16, further comprising adjusting said estimate of said remaining battery capacity based, at least in part, on a function of said remaining battery capacity measured over a period of time.

21. The method of claim 20 wherein said period of time is at least two weeks.

22. The method of claim 21 wherein said period of time is at least four weeks.

23. The method of claim 22 wherein said period of time is at least twelve weeks.

24. The method of claim 23 wherein said period of time is at least twenty-six weeks.

25. The method of claim 20 wherein said function is an average of a plurality of said remaining battery capacity measurements taken during said period of time.

26. The method of claim 16 wherein said measured battery parameter is a battery output voltage.

\* \* \* \* \*

UNITED STATES PATENT AND TRADEMARK OFFICE
CERTIFICATE OF CORRECTION

PATENT NO. : 8,452,395 B2
APPLICATION NO. : 12/830748
DATED : May 28, 2013
INVENTOR(S) : Ann M. Crespi Page 1 of 1

It is certified that error appears in the above-identified patent and that said Letters Patent is hereby corrected as shown below:

In the Claims:

Col. 10, line 9, delete "...instances of delivery of delivery of said relatively large pulse..." and insert in place thereof -- instances of delivery of said relatively large pulse --

Col. 10, line 52, delete "...instance of deliver..." and insert in place thereof -- instance of delivery --

Col. 10, line 64, delete "...instances of delivery of delivery of said relatively large pulse..." and insert in place thereof -- instances of delivery of said relatively large pulse --

Signed and Sealed this
Sixteenth Day of July, 2013

Teresa Stanek Rea
*Acting Director of the United States Patent and Trademark Office*